(12) United States Patent
Peter et al.

(10) Patent No.: US 8,041,414 B2
(45) Date of Patent: Oct. 18, 2011

(54) DUAL-MODALITY IMAGING

(75) Inventors: Joerg Peter, Schriesheim (DE); Michael Bock, Heidelberg (DE); Reiner Umathum, Heidelberg (DE)

(73) Assignee: DKFZ Deutsches Krebsforschungszentrum Stiftung Des Offentlichen Rechts, Heidelberg (DE)

( * ) Notice: Subject to any disclaimer, the term of this patent is extended or adjusted under 35 U.S.C. 154(b) by 367 days.

(21) Appl. No.: 12/440,129

(22) PCT Filed: Sep. 4, 2007

(86) PCT No.: PCT/EP2007/059232
§ 371 (c)(1),
(2), (4) Date: May 6, 2009

(87) PCT Pub. No.: WO2008/028904
PCT Pub. Date: Mar. 13, 2008

(65) Prior Publication Data
US 2009/0270718 A1    Oct. 29, 2009

(30) Foreign Application Priority Data
Sep. 6, 2006  (EP) .................................. 06120229

(51) Int. Cl.
*A61B 5/05* (2006.01)
(52) U.S. Cl. ........ 600/427; 600/407; 600/410; 600/420; 600/421; 600/422; 324/318; 324/322

(58) Field of Classification Search ............. 324/318, 324/322; 600/407, 410, 420, 421, 422, 427
See application file for complete search history.

(56) References Cited

U.S. PATENT DOCUMENTS
| | | | |
|---|---|---|---|
| 5,419,320 A | 5/1995 | Kawaguchi et al. | |
| 2004/0030238 A1 | 2/2004 | Vaughan | |

FOREIGN PATENT DOCUMENTS
| EP | 1 304 070 A2 | 4/2003 |
|---|---|---|
| EP | 1 559 363 A2 | 8/2005 |
| JP | 2004/202258 A | 7/2004 |
| WO | WO-98/30889 A1 | 7/1998 |
| WO | WO-2006/111485 A2 | 10/2006 |
| WO | WO-2006/111486 A1 | 10/2006 |

OTHER PUBLICATIONS
Masciotti et al.; "Combined Optical Tomographic and Magnetic Resonance Imaging of Tumor Bearing Mice"; Proc. SPIE, vol. 5693, pp. 74-81, 2005.

(Continued)

*Primary Examiner* — Brian Casler
*Assistant Examiner* — Joel Lamprecht
(74) *Attorney, Agent, or Firm* — Birch, Stewart, Kolasch and Birch, LLP

(57) ABSTRACT

The invention relates to a dual-modality imaging system and a method for dual-modality imaging of an imaged object, wherein a magnetic resonance imaging (MRI) apparatus for acquiring MRI data and at least one optical imaging detector for acquiring optical imaging data are arranged to acquire the MRI data and the optical imaging data of the imaged object (10) simultaneously, the at least one optical imaging detector being a non-contact optical imaging detector.

15 Claims, 10 Drawing Sheets

OTHER PUBLICATIONS

Hsiang et al.; "Coregistration of Dynamic Contrast Enhanced MRI and Broadband Diffuse Optical Spectroscopy for Characterizing Breast Cancer", Technology in Cancer Research & Treatment, vol. 4, pp. 549-558, 2005.

Siegel et al., "Temporal Comparison of Functional Brain Imaging with Diffuse Optical Tomography and FMRI During Rat Forepaw Stimulation", Phys. Med. Biol. 48, pp. 1391-1403, 2003.

Xu et al., "Magnetic-Resonance-Imaging-Coupled-Broadband Near-Infrared Tomography System for Small Animal Brain Studies", Applied Optics, vol. 44, No. 11, pp. 2177-2188, 2005.

Ntziachristos et al., "MRI-Guided Diffuse Optical Spectroscopy of Malignant and Benign Breast Lesions", Neoplasia, vol. 4, No. 4, pp. 347-354, 2002.

Hayes et al., "An Efficient, Highly Homogeneous Radiofrequency Coil for Whole-Body NMR Imaging at 1.5T", Journal of Magnetic Resonance 63, pp. 622-628, 1985.

Majors et al., "A Combined Confocal and Magnetic Resonance Microscope for Biological Studies", Review of Scientific Instruments, vol. 73, No. 12, pp. 4329-4338, 2005.

Schulz et al., Molecular Imaging, vol. 4, No. 2, pp. 373, 2005.

DUAL-MODALITY IMAGING

FIELD OF THE INVENTION

The present invention relates to a dual-modality imaging system and a method for dual-modality imaging using a magnetic resonance imaging (MRI) apparatus for acquiring MRI data and at least one optical imaging detector for acquiring optical imaging data.

BACKGROUND OF THE INVENTION

The qualitative and quantitative acquisition of morphological, functional and biochemical parameters using imaging methods is the basis for a plurality of medical research and application areas. Two known imaging methods are magnetic resonance imaging (MRI) and optical imaging techniques.

Magnetic resonance imaging (MRI) or nuclear magnetic resonance (NMR)[1] is an existing powerful non-invasive medical imaging technique for producing three-dimensional cross-sectional images to visualize the inside of living organisms. It is primarily used to demonstrate pathological or other physiological alterations of living tissues. In short, medical MRI relies on the relaxation properties of excited hydrogen nuclei in water. When the object to be imaged is placed in a strong (several Tesla) uniform magnetic field the spins of the atomic nuclei with non-zero spin quantum numbers align parallel or anti-parallel to the magnetic field. The imaged object is then briefly exposed to radio frequency (RF) pulses in a plane perpendicular to the magnetic field, causing the magnetization to leave its equilibrium state. The precessing magnetization creates an altering flux in a nearby coil, the magnitude and phase of which are the MRI signal. In order to selectively image different locations of the object (i.e. spatial encoding of the signal phase), orthogonal magnetic field gradients are applied, and this data represents the spatial frequencies of the imaged object. Tomographic images can be reconstructed from the acquired data using e.g. the discrete Fourier transform.

[1] NMR generally is referred to the investigation of natural occurring frequency differences within a sample of probe chemical environment whereas MRI refers to the application of externally controlled frequency differences within a sample to probe water (proton) distribution.

In clinical practice, MRI is used to distinguish between tissues (e.g. pathologic tissue such as a tumor from normal tissue) exploiting the different magnetic properties of tissue: decay times (transverse relaxation time, $T_2$, caused by the intrinsic spin-spin interaction; longitudinal relaxation, $T_1$, the spin-lattice relaxation time), and proton density. From these, physiological tissue parameters such as diffusion, perfusion, etc. can be derived.

Further imaging methods for in-vivo examination of biological processes known in the state-of-the-art are optical imaging techniques including fluorescence and bioluminescence imaging. Fluorescence is the result of a process that occurs in certain molecules called fluorophores or fluorescent dyes. A fluorescent probe is a fluorophore designed to localize within a specific region of a biological specimen or to respond to a specific stimulus. In order to perform fluorescence imaging, a photon of certain energy is supplied by an external source such as an incandescent lamp or a laser and absorbed by the fluorophore, creating an excited electronic singlet state. This process distinguishes fluorescence from bioluminescence. It follows that another photon of lower energy is emitted, returning the fluorophore to its ground state. Using an appropriate sensor device, the emitted photons can be detected. Bioluminescence refers to the visible light emission in living organisms that accompanies the oxidation of organic compounds (luciferins) mediated by an enzyme catalyst (luciferase). Unlike fluorescence approaches, the imaged object does not need to be exposed to the light of an external light source. Bioluminescence imaging is carried out by tagging cells with a luciferase gene. These genetically engineered, light emitting cells can be followed throughout the imaged object by means of an appropriate sensor device. At present, fluorescence appears to be more generalizable, compared with bioluminescence imaging. Bioluminescence is more limited to genes and proteins. Its advantage is the use of an inserted reporter gene that can be tailored to specific processes.

Optical imaging has evolved into a potentially valuable tool for assessing functional properties. Examples include protein-protein interactions with cells, gene regulation at the transcription level, protein degradation over time, enzymatic activity associated with tumor progression, and cell death. Examples of ongoing applications include cancer, inflammatory disease, neurodegenerative disease, gastrointestinal physiology, renal physiology, cell trafficking, stem cell research, transplant science, and muscle physiology.

Optical planar imaging and optical tomography (OT) are emerging as alternative molecular imaging modalities, that detect light propagated through tissue at single or multiple projections. In the near future, optical tomography techniques are expected to improve considerably in spatial resolution by employing higher-density measurements and advanced photon technologies, e.g. based upon modulated intensity light or very short photon pulses. Clinical optical imaging applications will require high efficient photon collection systems. Primary interest for using an optical imaging technique lies in the non-invasive and non-hazardous nature of optical photons used, its low cost, its straightforward technology and most significantly in the availability of activatable probes that produce a signal only when they interact with their targets—as compared to radiolabelled probes used in PET (positron emission tomography) and SPECT (single photon emission computed tomography), which produce a signal continuously, independent of interacting with their targets, through the decay of the radioisotope. In OT, images are influenced greatly by the spatially dependent absorption and scattering properties of tissue. Boundery measurements from one or several sources and detectors are used to recover the unknown parameters from a transport model described, for instance, by a partial differential equation. The contrast between the properties of diseased and healthy tissue can be used in clinical diagnosis.

In the state of the art optical imaging detectors are known either to employ photo detector devices, e.g. CCD cameras, which are placed at a certain distance from, but not in contact with the imaged object, or to employ fibre-optics which bring the detector in contact with the imaged object.

The majority of existing optical imaging approaches are using CCD cameras. CCDs (charge coupled devices) are charge coupled imaging sensors that serve for highly sensitive detection of photons. The CCD camera is divided into a multiplicity of small light-sensitive zones (pixels) which produce the individual pixels of a two-dimensional image. The number of electrons is measured in each pixel, with the result that an image can be reconstructed. CCDs should be cooled since otherwise more electrons would be read out which would not be liberated as a result of the light incidence but rather as a result of heating. In order to define an optical field-of view, the CCD detector is typically coupled to a lens.

Almost all of the commercially available CCD based imaging designs generate only planar images of the integrated light distribution emitted from the surface of the imaged object, e.g. an animal. Market leader in the small animal optical imaging instrumentation arena is Xenogen Corp. Alameda, USA. The principle design of known CCD based optical imaging systems as used for in vivo fluorescence and bioluminescence imaging comprises a CCD camera, which is arranged at a certain distance to the imaged object (non-contact measurement) and aimed at this object in order to detect photons emitted from the object. Since CCD detectors need to be equipped with a lens which does impose a minimal focal length CCD cameras tend to be rather bulky instruments yielding large imaging compartments. If eventually used for tomographic imaging, a CCD-based camera system needs to be rotated around the imaged object in order to collect projection views or a multitude of cameras needs to be used in parallel. In another potential application lens-based CCD camera systems of the prior art cannot be positioned within the field-of-view of another imaging modality with the purpose of dual-modality image acquisition such as positron emission tomography (PET) for simultaneous PET/optical imaging.

Known fibre optics based optical imaging designs are being used in a way that the fibre ending tips are placed in contact with the object to be imaged. One of the reasons is that a particular fibre ending tip does not have a distinct well-defined field-of-view which would allow for backtracking a photon's incoming direction. In order to be resolvable for imaging, the imaged object, such as a mouse, needs to be put into a preferably cylindrical compartment which is filled with an appropriate liquid having specific optical properties. This is considered a significant drawback because of animal handling issues, experimental complexity and study management.

In the two pending international applications PCT/EP2006/061474 and PCT/EP2006/061475, a novel microlens array based optical imaging detector and a dual-modality imaging concept with a combination of positron emission tomography (PET) and optical imaging are described.

In the state of the art MR imaging and optical imaging are two imaging techniques, which are usually applied separately, using two separate devices successively. Although optical tomography provides functional and molecular information with a very high sensitivity, a major problem in optical imaging is its low spatial resolution and, hence, a lack of anatomical information. This problem which is also known for PET and single photon emission computer tomography (SPECT) imaging is amplified in optical tomography even more, when activatable probes are used that create no background. The generated signal has, if at all, only a weak correlation with surrounding morphological structure, especially in applications with novel, very specific tracers or cell trafficking studies. Thus, PET and SPECT scanners are nowadays often combined with CT, PET, and recently with MRI, to provide anatomical and functional information at the same time. While (at the current state of the art) CT provides excellent contrast for bone structures, magnetic resonance imaging (MRI) yields excellent soft tissue contrast. Therefore and for its illustrated highly complementary use in medicine/research, it would be desirable to combine the diagnostic benefits of an optical imaging scanner with those of an MRI scanner. While morphological imaging procedures such as magnetic resonance imaging in general have difficulties differentiating viable tumor from tumor necrosis or scar tissue, functional/molecular data such as those provided by optical imaging typically support only limited anatomical information which makes it difficult to render the accurate localization of the lesion.

The co-registration of sequentially acquired optical and MR images is described e.g. in Masciotti, J; Abdoulaev, G et al., "Combined optical tomographic and magnetic resonance imaging of tumor bearing mice", Proc. SPIE, Vol. 5693, pp. 74-81, 2005; Springett H. Dehghani B W, et al. "Coregistration Of Dynamic Contrast Enhanced MRI and Broadband Diffuse Optical Spectroscopy for Characterizing Breast Cancer", Technology in Cancer Research & Treatment, vol. 4, pp. 549-558, 2005; Siegel A M, Culver JP et al. "Temporal comparison of functional brain imaging with diffuse optical tomography and FMRI during rat forepaw stimulation", Phys. Med. Biol., vol. 48, pp. 1391-1403, 2003, which illustrates the desire to achieve combined optical and MR images.

A comparison of the images obtained by the two sequentially applied imaging methods is possible only to a limited extent since they cannot be obtained simultaneously. The problems of excessive and prolonged burdening of the subject to be examined, the non-reproducibility of kinetic studies, the non-identical imaging geometries, animal and organ movement and the correct superposition of the images arise, when the two methods are carried out successively.

EP 1 559 363 A2 refers to an apparatus for providing optical and anatomical diagnostic imaging. The apparatus comprises an anatomical imaging unit for inserting into a body cavity, wherein the anatomical imaging unit acquires anatomical images of the body cavity and an optical imaging unit substantially enclosed within a substantially translucent portion of the anatomical imaging unit, wherein the optical imaging unit detects fluorescence in the body cavity. According to one embodiment, the anatomical imaging unit comprises a magnetic resonance imaging component for acquiring magnetic resonance images of the body cavity.

Paul D. Majors et al.: "A combined confocal and magnetic resonance microscope for biological studies", Review of Scientific Instruments, vol. 73, no. 12, pages 4329-4338 describes a novel microscope for studying live cells simultaneously with both confocal scanning laser fluorescence optical microscopy and magnetic resonance microscopy.

Combined optical/MR imaging systems, where the optical detector is in contact with the imaged object, have been described recently [Xu H, Springett, R et al., "Magnetic-resonance-imaging-coupled broadband near-infrared tomography system for small animal brain studies", Applied Optics, vol. 44, pp. 2177-2188, 2005; Ntziachristos V, Yodh AG, et al., "MRI-Guided Diffuse Optical Spectroscopy of Malignant and Benign Breast Lesions" Neoplasia, vol. 4, pp. 347-354, 2002]. While such setup is well suited for basic experimental (phantom) studies, contact imaging has significant limitations since fiber-based detection leads to insufficient spatial sampling and field-of-view, and further constraints on the reconstruction algorithm. Moreover, positioning and contact issues which mostly are coped with by using matching fluids complicate experimental procedures and contribute to unnecessary photon diffusion and light attenuation.

SUMMARY OF THE INVENTION

Therefore, the present invention is based on the object of avoiding the disadvantages of the prior art and of combining the advantages of the two techniques of magnetic resonance imaging (MRI) and optical imaging.

This object is achieved by means of a dual-modality imaging system, wherein a magnetic resonance imaging (MRI) apparatus for acquiring MRI data and at least one optical imaging detector for acquiring optical imaging data are arranged to acquire the MRI data and the optical imaging data of an imaged object simultaneously, the at least one optical imaging detector being a non-contact optical imaging detector.

Dual-modality MR/OT imaging as proposed by the present invention generates accurately merged functional/molecular and morphological data sets in a single examination session, thus overcoming the limitations of separate image acquisition.

The present invention further solves problems connected to separately imaging optical and NMR signals, as for instance
- direct study and comparison of tracer/marker kinetics of optical and NMR induced signals which might be bound to specific molecular processes
- image registration artifacts of sub-modality scans
- individual tracer kinetics and time-resolved concurrent data analysis
- animal handling and study length
- animal/organ movement
- problem of subject encumbrance which are inaccessible (kinetics) or become crucial (coregistration, animal management).

With the present invention, a single-procedural, time-resolved, non-contact imaging of in vivo distributions of fluorescent or bioluminescent optical probes (OT) and simultaneous detection of nuclear magnetic resonance (NMR) signals in a small object, e.g. in mice and rats, or portions thereof, such as the brain, but potentially also in specific human organs and tissues such as the human brain is possible. The invention assesses visual representation, characterization and quantification of functional and/or molecular biological processes at the cellular and sub-cellular levels (primarily through the optical signal) and anatomical structures (primarily through the MR signal) within intact living organisms by means of a simultaneously performed image acquisition procedure. The invention provides an imaging system that is highly sensitive in identifying location, magnitude and time variation of specific molecular events (e.g. gene expression and enzyme activity) by simultaneously detecting optical markers in vivo while, with the same acquisition procedure, this spatially low-resolution (generally $\geq 500$ μm) optical information is superimposed with the spatially high-resolution (generally $\leq 50$ μm) anatomical details of the imaged object, improving diagnostic accuracy of optical imaging by magnetic resonance imaging.

Some preferred applications of the dual-modality imaging system according to the invention are to detect and state tumors, to image specific cellular and molecular processes (e.g. gene expression, or more complex molecular interactions such as protein-protein interactions), to monitor multiple molecular events simultaneously, to track single or dual-labelled cells using reporter genes or dual-modal labels visible to both optical and MR imaging, to optimize drug and gene therapy, to image drug effects at a molecular and cellular level, to assess disease progression at a molecular pathological level, especially to create the possibility of achieving all of the above goals of imaging in a single, rapid, reproducible, and quantitative manner.

Further uses of the present invention comprise monitoring time-dependent experimental, developmental, environmental and therapeutic influences on gene products in the same animal (or patient), studying the interaction of tumor cells and the immune system, studying viral infections by marking the virus of interest with a reporter gene, and many others. There is also an enormous clinical potential for the non-invasive assessment of endogenous and exogenous gene expression in vivo (gene (DNA), message (RNA), protein, function), for imaging receptors, enzymes, transporters, for novel applications in basic and translational research (gene therapy, etc.), for early detection of disease, for guidance for therapeutic choices, for monitoring drug action, for aid of pre-clinical drug development, for non-invasive and repetitive monitoring of gene therapy, and for optimizing clinical trials of human gene therapy.

An optical imaging detector in the context of the present invention is a device capable of acquiring images of at least part of an imaged object by detecting fluorescent or bioluminescent signals (i.e. light) emitted from the imaged object. The imaged object can be any object known by those skilled in the art, which is accessible by optical imaging. Preferably the imaged object is an intact living organism like a small animal or sections of a human being such as breast or head.

Another advantage of the dual-modality imaging system according to the present invention is that the at least one optical imaging detector is designed as a non-contact detector. According to the present invention, the detector is not in contact with the imaged object, unlike known fibre-optics based optical imaging design with fibre ending tips being placed in contact with the object. The non-contact optical detector of the present invention has significant advantages in view of simplifying the handling of the imaged object (e.g. a living animal), reducing the experimental complexity and simplifying the study management.

In a preferred embodiment of the present invention, the MRI apparatus comprises an imaging magnet to produce a static magnetic field within an imaging volume of the MRI apparatus, gradient coils to produce gradient magnetic fields to superimpose the static magnetic field within the imaging volume and at least one RF coil, which is arranged within the imaging volume to surround the imaged object, at least a subsystem of the at least one optical imaging detector being arranged within the imaging volume to detect photons (fluorescence or bioluminescence signals) emitted by the imaged object through a recess of the RF coil.

An imaging magnet, gradient coils and an RF coil are conventional hardware components of an MRI apparatus. The imaging magnet is used to produce a static magnetic field Bo within an imaging volume of the MRI apparatus. The imaging magnet is preferably selected from the group of resistive magnet, permanent magnet and superconducting magnet. The magnetic field of the imaging magnet should be as homogeneous as possible. The gradient coils are usually positioned within the imaging magnet and are used to produce gradient magnetic fields to superimpose the static magnetic field within the imaging volume, so that a selective spatial excitation can occur within the imaging volume within the gradient coils. The RF coil is arranged within the gradient coils within the imaging volume to surround an object to be imaged. The RF coil is used to transmit and/or receive an RF signal to and/or from the imaged object. The RF coil used for the dual-modality imaging system according to the present invention, which is placed within the magnetic field produced by the imaging magnet and the gradient coils, is preferably a transmit/receive coil which is used for both spin excitation and signal detection or is designed as a receive coil for a signal detection only. If the RF coil is a receive coil, a spin excitation is accomplished with another external RF coil such as through the use of the body resonator in a clinical MRI system. Desirable properties of the RF coil(s) which work as an RF interface between the sample spins and the MRI system include a homogeneous distribution of the generated RF field across the entire object space, good transmission power efficiency and high signal detection sensitivity.

The RF coil which can be used for the dual-modality imaging system according to the present invention to surround the imaged object can be a surface coil or a volume coil. A surface coil rests on the surface of the object to be imaged. It usually comprises one or more loops of a conductive wire and is looped around the imaged object. Volume coils are large enough to fit the whole imaged object, which can be e.g. the whole body of an animal to be imaged or a specific region, such as the head or a limb. The most commonly used design of a volume coil is a birdcage coil. Any appropriate RF coil design can be used for the purpose of the invention as long as it provides recesses, through which a non-contact optical imaging detector can receive the fluorescence or luminescence photons emitted from the imaged object.

The at least one optical imaging detector or at least a subsystem of the at least one optical imaging detector is preferably arranged within the imaging volume to detect photons (fluorescence or bioluminescence signals) emitted by the imaged object through such a recess of the RF coil. For example, the optical imaging detector or a subsystem of the optical imaging detector can be integrated into an opening of the RF coil.

The imaging volume is in the context of the present invention the volume within the imaging magnet and within the gradient coils, where the static magnetic field of the imaging magnet and the gradient fields of the gradient coils are superimposed. This imaging volume contains an object space, where the object to be imaged is to be placed and which is positioned within the RF coil(s). The imaging volume of the MRI apparatus used for the dual-modality imaging system according to the invention must be large enough to accommodate the RF coil and at least a subsystem of the optical imaging detector. For example, a wide bore clinical MRI apparatus can be used for the present invention.

A recess of the RF coil is in the context of the present invention any region of the RF coil, which is able to transmit light emitted from the imaged object, especially fluorescence or luminescence signals. The recess can e.g. be an opening between the electrically conductive wires of the RF coil or any region of the RF coil filled with a material which essentially does not absorb luminescence or fluorescence photons emitted by the imaged object.

According to a preferred embodiment of the present invention, at least a subsystem of the optical imaging detector is integrated into the at least on RF coil forming a module, which is permanently integrated into the MRI apparatus or which is removably combined with the MRI apparatus.

According to a preferred embodiment of the present invention, the MRI apparatus of the dual-modality imaging system contains an RF coil, which has a birdcage coil design. The birdcage coil design [Hayes C E, Edelstein W A, et al. "An efficient, highly homogeneous radiofrequency coil for whole-body NMR imaging at 1.5T." J Magn Reson, 63:622-628, 1985] constitutes present art in small animal imaging and is ideally suited for MRI experiments because it generates a homogeneous magnetic field within the coil region at high frequencies. It also allows for a straightforward arrangement with the optical detector sub-system.

A birdcage coil comprises circular end rings connected by a number of straight segments (which are preferably equally spaced), each of the straight segments including a capacitance (preferably fixed and adjustable capacitors, which are used for tuning the resonance frequency of the RF coil). A preferred birdcage design, which can be used for the present invention, contains electrically conductive circular end rings connected by electrically conductive straight segments (e.g. made of copper foils), which are mounted on a non-conductive support shaped like a tube (e.g. an epoxy resin tube). This tube preferably contains gaps, which are positioned adjacent to the electrically conductive elements, the gaps forming recesses of the RF coil. Exemplarily, the tube can have an outer diameter of 52 mm and an axial length of 100 mm with gap sizes of 6 mm×80 mm axially. In an exemplary embodiment, the bird cage coil comprises 12 straight segments, and two circular end rings.

According to a preferred embodiment of the present invention, the dual-modality imaging system comprises at least one optical imaging detector, which comprises a micro-lens array with a plurality of micro-lenses. Such an optical imaging detector is described in the pending international application with the application No. PCT/EP2006/061475, which is hereby incorporated by reference herein. The micro-lenses of the micro-lens array are arranged to collimate light emitted from the imaged object onto a photo detector or (for certain applications) to project light towards the imaged object onto a part of the object to be imaged. By using an array of micro-lenses a position sensitivity can be achieved.

Each micro-lens has preferably a diameter in the range from 0.1 to 2 mm. By way of example with a lens diameter of 1 mm and an overall array size of 1 cm×1 cm one micro-lens array assembles 100 lenses at 1 mm spatially separated lens pitch—which subsequently corresponds to the intrinsic spatial detection resolution of the optical system. The micro-lens array can for example have a square, rectangular or hexagonal pattern. An optical collimator can be positioned in front or behind of each micro-lens array with the purpose of averting light cross-talk between individual micro-lens detector pairs. Such an optical collimator is preferably a multi-hole collimator which is adapted to the micro-lens array.

When combining optical imaging and magnetic resonance imaging, one major challenge is to develop optical imaging detectors which can be used in a high magnetic field environment, susceptibility artifacts in the MRI data due to the presence of the optical imaging detector, and to eliminate electromagnetic interference effects between the optical and MR imaging systems which could cause artifacts in either modality. Therefore, it is necessary to implement an optical imaging detector which can operate without performance degradation in magnetic fields of several TESLA and which does not cause any noticeable distortion or artifacts in the MR images. Furthermore, the optical imaging detector or parts of it, which are placed within the magnetic field, ideally need(s) to be transparent for high frequency fields and should not create eddy currents as a result of high frequency and gradient fields. In turn, the high frequency fields should not impinge on the electronics of the optical imaging detector. Technical difficulties therefore include minimizing the use and optimizing the layout of conducting or ferromagnetic materials in the optical imaging detector front end, maintaining the homogeneity of the main magnetic field and minimizing electromagnetic interference between optical and nuclear magnetic resonance signals. In addition, there is a number of practical issues. The optical system must be compact to fit inside the relatively narrow bore of most MRI apparatuses, it must be easy to take in and out of the MRI apparatus and it must be accurately located relative to the MRI apparatus to permit direct image registration. The use of a micro-lens array as a subsystem of the optical imaging detector helps to comply with all of these issues. It can consist of a material suitable for the use within the magnetic field of the MRI apparatus, which essentially does not interfere with the MR imaging process, e.g. glass. The use of a micro-lens array allows a compact design of an optical imaging detector and provides a locally adaptive dynamic range of the optical system, if partitioned photo detectors such as fiber coupled photo detector arrays are used that allow for individual photo detector element read out.

Preferably, the dual-modality imaging system according to the present invention includes at least one optical imaging detector comprising a micro-lens array with a plurality of micro-lenses, the micro-lens array being integrated into the at least one RF coil. The micro-lens arrays are preferably positioned at the recesses of the RF coil. They can e.g. be integrated into the gaps between the straight segments of an RF coil with a birdcage design.

Preferably, the at least one optical imaging detector of the dual-modality imaging system according to the invention comprises at least one photo detector. A photo detector is a sensor, which is arranged to detect photons emitted from the imaged object. The photo detector comprises for example at least one CCD or at least one photo diode. Preferably the at least photo detector is a position sensitive photo detector, which detects photons and the position of their entering the photo detector. Examples for position sensitive photo detectors are a CCD (charge-coupled device) based detector, an APD (avalanche photo diode) array, a photo diode array, or a CMOS (complementary metal-oxide semiconductor) sensor.

An APD array or a photo diode array contains a plurality of APDs or photo diodes respectively, which is arranged in an array.

A CMOS (complementary metal oxide semiconductor) sensor is an active pixel sensor, which includes an array of photo sensitive diodes, one diode within each pixel. Each pixel has its own amplifier, allowing pixels to be read individually which leads to the position-sensitivity of the CMOS sensor.

The photo detector can either be located at the focal plane of a micro-lens array of the optical imaging detector or be connected to a micro-lens array of the optical imaging detector via optical fibers.

According to a first preferred embodiment of the present invention, each micro-lens of the micro-lens array is connected to an optical fiber. Preferably, the connection is achieved by providing a network of optical fibers which is mounted on a multi-hole plate such that the focal points of the individual micro-lenses correspond locally to single fiber ending points. Preferably, each micro-lens is connected to a photo detector element, e.g. a photo diode, or to a light source via an optical fiber. These optical fibers can take on two different purposes: Either the light collected by the micro-lenses will be tracked through the fibers to the photo detector elements for detection or light from a light source (e.g. a laser diode) is tracked through the fibers to the imaged object, e.g. for fluorochrome excitation. The advantage of this embodiment is that each fiber coupled photo detector element has its own individual dynamic range. Furthermore, the light collected by a micro-lens can be conveyed through the fiber to a photo detector which is located externally of the imaging volume (outside of the magnetic field).

For fluorochrome excitation, the optical imaging detector of the dual-modality imaging system according to the invention can comprise at least one light source arranged to illuminate at least part of the imaged object. For example, in fluorescence imaging the at least one light source illuminates at least part of the imaged object with light of an excitation wavelength in order to excite fluorescence probes within the imaged object, resulting in the stimulated emission of light with a shifted wavelength. Fluorescence mediated optical imaging requires a light source preferably of variable selectable wavelengths to be integrated into the imaging system for fluorochrome excitation. Guiding excitation light to the imaged object can be accomplished in several ways, one of which is the dual-use of optical fibers. Alternative means to accomplish the same can be adjustable mirrors placed in non-field-of-view areas of the photo detectors between the imaged object and the inner surface of the RF coil, e.g. the coaxial epoxy resin tube of the birdcage coil described above. Such mirrors can be translatable along the long axis of the imaged object to allow for arbitrary deflection and positioning of laser (or collimated) light. Another preferred embodiment of this invention comprises a multitude of (or at least one) cylindrical or pixelated (single spot array), collimated light source(s), which are placed adjacent at close proximity to the RF coil, e.g. the coaxial epoxy resin tube of the birdcage coil described above. Since the at least one light source can involve an optical fan beam collimator with variable fan beam solid angle, the generated light field can be adjusted to illuminate variously sized light fields, allowing for very focused or very uniform illumination of the imaged object, all of which is desired for a number of applications.

Preferably, the at least one light source is positioned outside of the RF coil, most preferably outside of the imaging volume. The light of the light source can be guided via at least one optical fiber of a fiber optic network to the imaged object. The majority of optical fibers not used for carrying excitation light from the light source to the imaged object is used for carrying emission light from the imaged object to at least one photo detector (preferably a plurality of photo detector elements) mirroring the number of micro-lenses in the micro-lens array. The photo detector is also preferably located outside the magnetic field.

The optical imaging detector of the dual-modality imaging system according to the invention can further comprise at least one filter anywhere in the optical transmission pathway from the imaged object to the optical detector, e.g. in front of each micro-lens array, for filtering out light of at least one light source. Such a filter can be provided e.g. for the purpose of filtering out laser excitation light, when the detector is used for fluorescence imaging. For bioluminescence imaging no filter is needed. The filter is preferably removable or replaceable. Different filters can be used for different optical probes/markers needing excitation light of a specific wavelength which requires appropriate filter arrangements.

According to a second preferred embodiment of the present invention, the at least one optical imaging detector of the dual-modality imaging system comprises a micro-lens array and a position-sensitive photo detector, which is positioned at the focal plane of the micro-lens array. Such an optical imaging detector is described in the pending international application with the application No. PCT/EP2006/061475, which is hereby incorporated by reference herein. In this case no optical fibers are needed to transfer photons from the micro-lenses of the micro-lens array to the photo-detector, thus simplifying the detector construction. The position-sensitive photo detector is preferably a large field photo detector. This photo detector can e.g. be a CCD, an APT array, a photo diode array, a CMOS, or any other position-sensitive light detector. In a preferred embodiment, a CMOS sensor is used for its performance (sensitivity, noise characteristics, time resolution, etc.) and cost. The photo detector is being used for the purpose of transforming the incoming light into an electrical signal. Since position-sensitive photo detectors consist in general of a two-dimensional lattice of individual photo detector elements, the size and, more importantly, the pitch of the photo detector element should be selected equal to, or a multiple of, the micro-lens size and pitch, respectively.

The photo detectors of the optical imaging detector used for the present invention can be radially relocatable in relation to the imaged object. A minimal radial position (e.g. an inner radius) of the photo detectors is determined by the RF coil dimensions. A design with an increased radial displacement of the photo detectors can reduce artifacts, if any are imposed by the material of the photo detectors onto the MRI apparatus.

The signal detected by the at least one photo detector can either be directly used for density distribution evaluation or, when incorporating the projection signals of all planar optical detection areas, can be further processed by a mathematical image reconstruction procedure which produces tomographic transversal slices through the object carrying (possibly quantitative) information about the internal signal density of a specifically labelled chemical compound within the imaged object.

The present invention furthermore relates to a non-contact (preferably three-dimensional) optical imaging method for dual-modality imaging of an imaged object, wherein magnetic resonance imaging data and optical imaging data of the imaged object are acquired simultaneously by a magnetic resonance imaging apparatus and a non-contact optical imaging detector. The design and function of the MRI apparatus and the optical imaging detector(s) used for this method can be similar to the ones described above. This method preferably includes the steps of reconstructing an MR image and an optical image by the acquired MRI data and optical imaging data and displaying at least one of the MR image, the optical image or a fused MR/optical image on a display device.

The present invention is advantageously directed towards a dual-modality imaging system, wherein an optical imaging detector which is not in contact with the image object is combined with a magnetic resonance imaging (MRI) device to allow both types of data to be collected simultaneously, wherein the imaging data is not detrimentally effected by the magnetic fields produced by the MRI apparatus and the MRI data is not detrimentally effected by the optical imaging detector, at least subsystems of which are positioned within the imaging volume. The major advantages of the present invention are:

simultaneous acquisition of high quality data,
compact design allowing for the construction of a simple insert,
near-perfect registration,
high-resolution anatomical context for non-contact-in vivo optical imaging (e.g. optical tomography),
the optical imaging detector is able to withstand high magnetic fields (specifically when a micro-lens array is placed within the magnetic fields and connected to a photo detector outside of the magnetic fields via optical fibers) and
minimal MR susceptibility artifacts due to the optical imaging detector (specifically when a micro-lens array is placed within the magnetic fields and is connected to a photo detector outside of the magnetic fields via optical fibers).

Since both regional distribution and time variation of the underlying multi-variate optical photon emission distributions as well as MR signals are acquisition and subject specific and diversified by variations thereof, and imaging procedures cannot be performed repeatedly at short time intervals on the same living object in many cases, combined and simultaneous imaging is desired and possible with this novel device carrying clearly advantageous potential. Further advantages are simultaneous recording of tracer kinetics, imaging of multiple distinctive molecular processes as part of an investigated molecular pathway, less subject encumbrance, and identical imaging geometries. The proposed dual-modality tomographic imaging system has the potential to accurately quantify fluorescence and/or bioluminescence distributions in deep heterogeneous media in vivo at high spatial resolution and in correlation to the anatomy of the imaged object provided by MRI.

The present invention is explained in greater detail below with reference to preferred embodiments shown in the drawing.

DETAILED DESCRIPTION OF THE FIGURES

Figure 1:
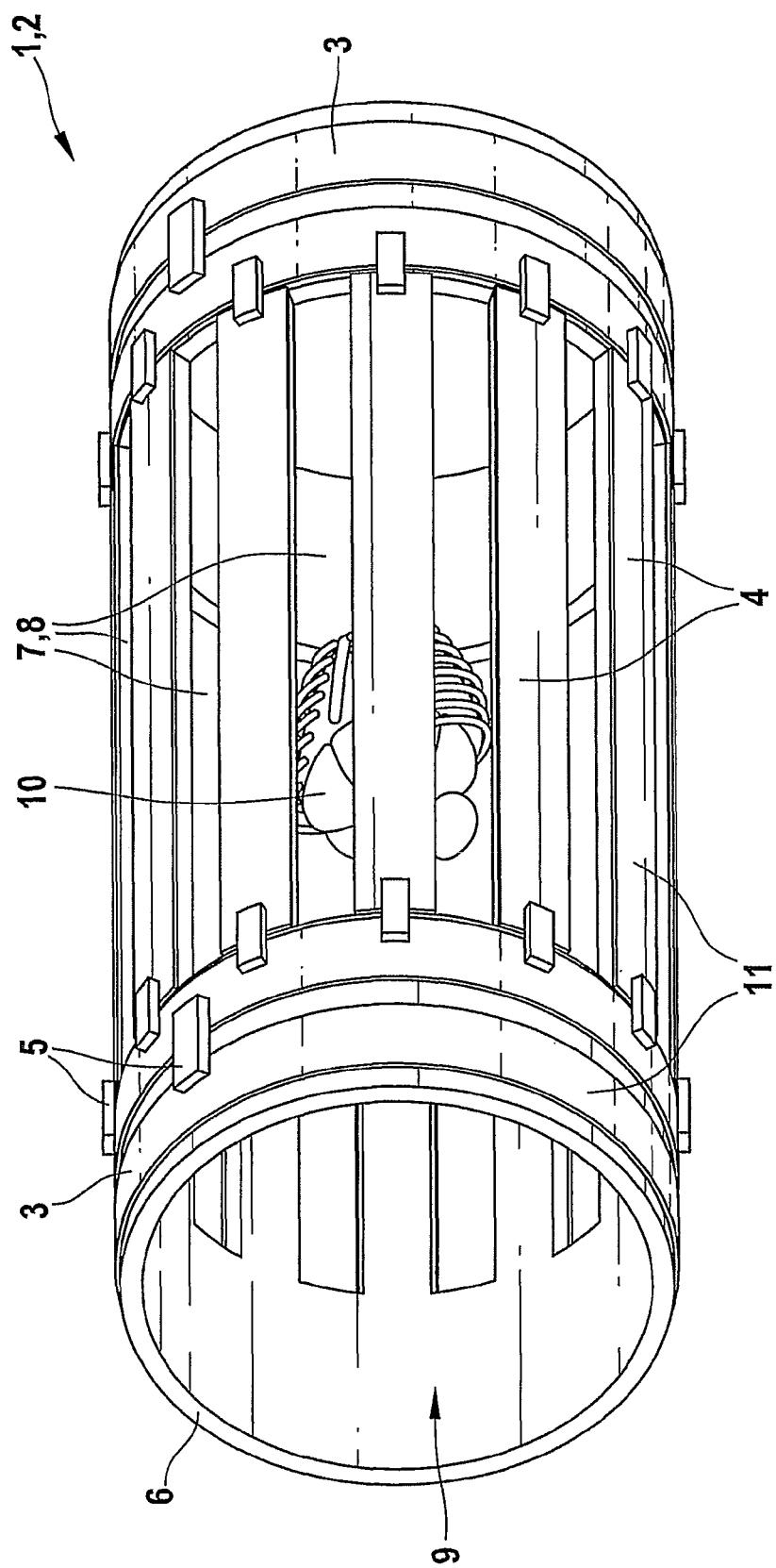
FIG. 1 shows a birdcage coil design of an RF coil, which can be used within the MRI apparatus of an embodiment of the dual-modality imaging system according to the present invention.

FIG. 1 shows a birdcage coil design of an RF coil, which can be used within the MRI apparatus of an embodiment of the dual-modality imaging system according to the present invention.

The RF coil 1 with a birdcage coil design 2 comprises two circular end rings 3, which are connected by a number of straight segments 4. The straight segments 4 are equally spaced. A number of capacitors 5 is connected to the circular end rings 3 and the straight segments 4. These electrically conductive elements 11 are made of a metal foil, e.g. a copper foil. The circular end rings 3 and the straight segments 4 are mounted on a support 6, which is shaped like a tube and is made of a non-conductive material, e.g. epoxy resin. The support 6 contains gaps 7 which are positioned adjacent to the electrically conductive elements 11, in particular gaps 7 are positioned between the straight segments 4. In order to form these gaps 7, areas of the tube have been removed, e.g. to allow an optical imaging detector or subsystems of an optical imaging detector (e.g. micro-lens arrays) to be mounted. The gaps 7 are recesses 8 through which photos emitted by an imaged object 10 within the object space 9 can reach an optical imaging detector (not shown) outside of the RF coil 1. The support 6 can e.g. have an outer diameter of 55 mm, an axial length of 100 mm with gaps 7 each having a size of 6 mm×80 mm.

Figure 2:
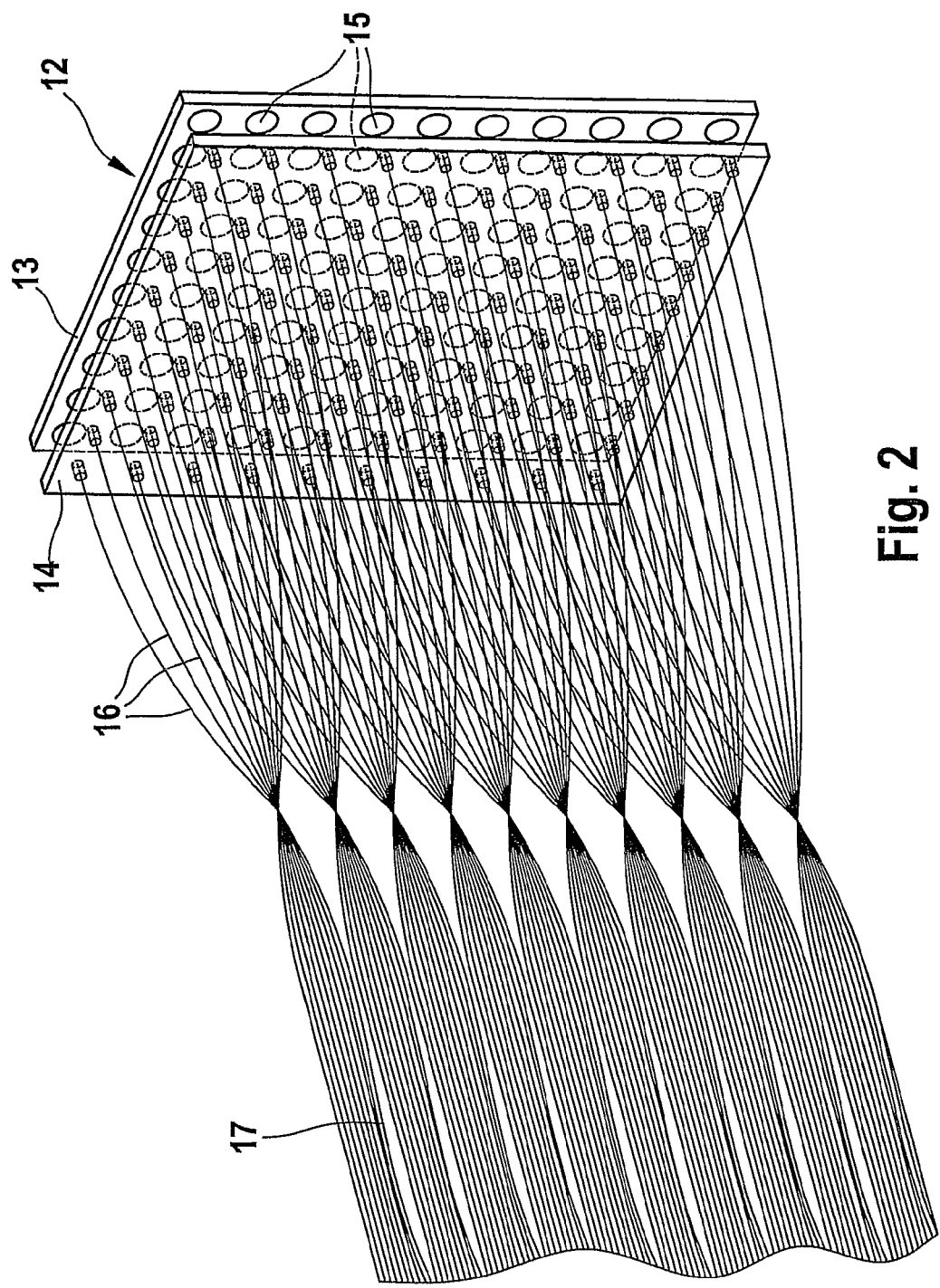
FIG. 2 shows a micro-lens array with fibers connected to the micro-lenses, which can be used in an embodiment of the dual-modality imaging system according to the present invention.

FIG. 2 shows a micro-lens array with fibers optically connected to the micro-lenses, which micro-lens array can be used in an embodiment of the dual-modality imaging system according to the present invention.

The micro-lens array 12 (in a square pattern 13) contains a multi-hole plate 14 and a plurality of mounted micro-lenses 15. A network of optical fibers 16 is mounted on a multi-hole plate 14 such that the focal points of the individual micro-lenses 15 correspond locally to single fiber ending points. The optical fibers 16 merge into a fiber bundle 17. Depending upon the user-selectable operation of the micro-lens array 12, each individual unit of a micro-lens 15 connected to an optical fiber 16 can take on one of two purposes. Either light collected by the micro-lens 15 will be converged through its assigned optical fiber 16 for detection to a photo detector (not shown), e.g. a photo diode, which is preferably located outside of the magnetic field of the MRI apparatus (not shown), or light from a light source (not shown), e.g. a laser diode, will be guided to the imaged object within the MRI apparatus (not shown) for fluorochrome excitation.

Figure 3A:
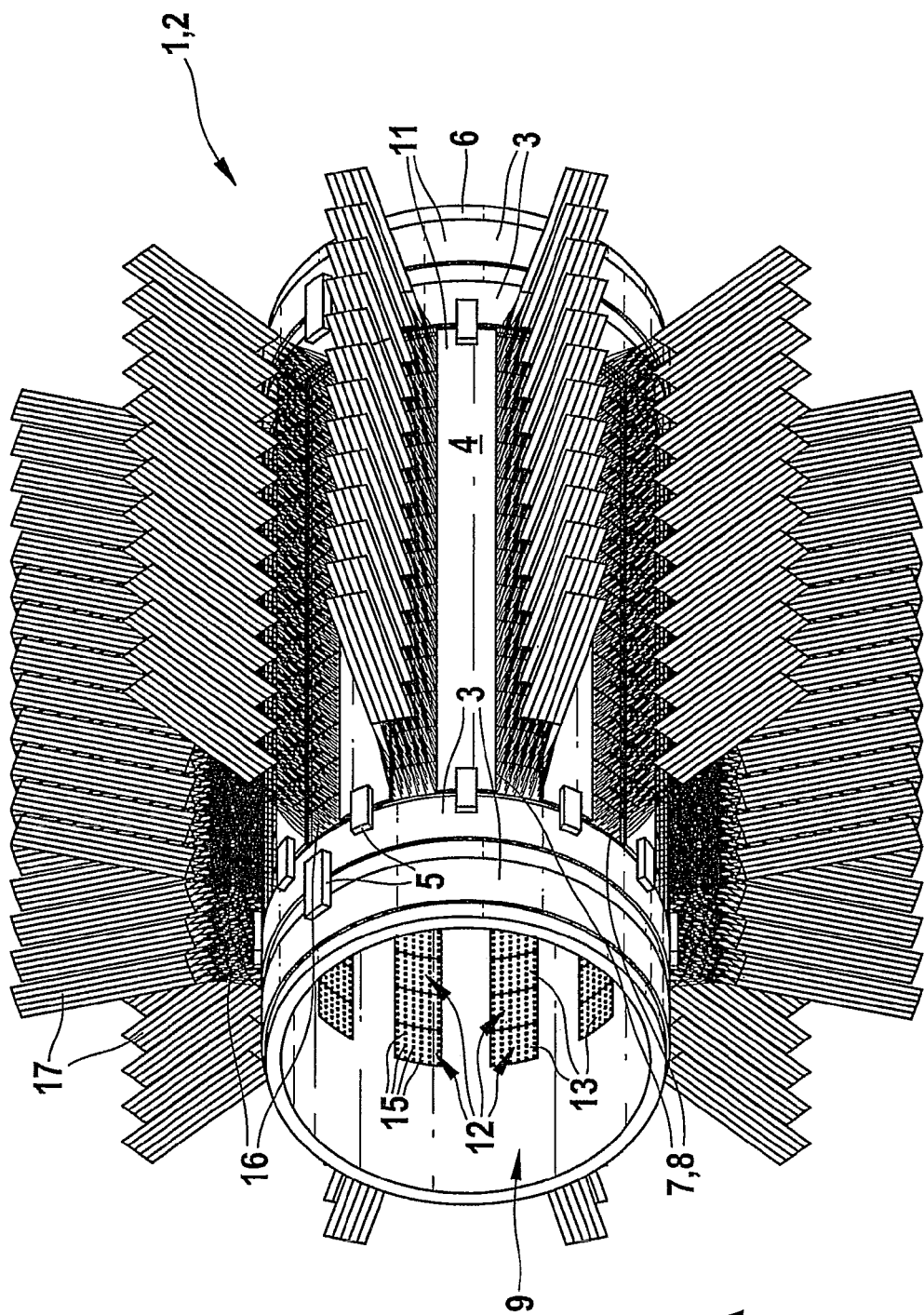
FIGS. 3A and 3B show schematically a perspective view and a transaxial view of a section of a first embodiment of the dual-modality imaging system according to the invention with micro-lens-arrays, the micro-lenses of which are connected to optical fibers.

FIG. 3A shows schematically a perspective view of a section of a first embodiment of a dual-modality imaging system according to the invention with micro-lens arrays, the micro-lenses of which are connected to optical fibers.

The shown section is part of the dual-modality imaging system, wherein an MRI apparatus for acquiring MRI data and optical imaging detectors for acquiring optical imaging data are arranged to acquire MRI data and the optical data of an imaged object (not shown) simultaneously, the optical imaging detectors being non-contact optical imaging detectors. In FIG. 3A, an RF coil 1 (in a birdcage coil design 2 according to FIG. 1) which is part of the MRI apparatus is shown.

In this dual-modality imaging system according to the invention, this RF coil 1 is placed within the imaging volume of the MRI apparatus inside of an imaging magnet (not shown) and of gradient coils (not shown). The RF coil 1 is arranged to surround an imaged object, which is placed within the object space 9 inside of the RF coil 1. Micro-lens arrays 12, which are subsystems of the optical imaging detectors, are arranged within the imaging volume of the MRI apparatus to detect fluorescence or bioluminescence photons emitted by an imaged object through the recesses 8 (gap 7) of the RF coil 1. More precisely, the micro-lens arrays 12 of the optical imaging detectors are integrated into the RF coil 1. They are located within the gaps 7 (of the support 6) between the straight segments 4 of the RF coil 1. By way of example, micro-lens arrays 12 with an overall object facing size of 6 mm×6 mm are implemented. In a preferred embodiment, each of the micro-lens arrays 12 consists of an array of 6×6 microlenses 15 of 1 mm in diameter each. A plurality of micro-lens arrays 12 is placed side by side to fill a gap 7 of the RF coil support 6, commonly referred to as a planar optical detection area. For a preferred lens size of 1 mm one micro-lens array 12 assembles 36 lenses 15 allowing for a 1 mm spatially separated lens pitch—which subsequently correspond to the spatial intrinsic detection resolution of the optical imaging system. If a higher spatial resolution is desired, the micro-lens diameter can be varied accordingly. Given the geometry of the exemplarily chosen birdcage RF coil 1, there are twelve gaps 7 which are filled with micro-lens arrays 12 yielding, by way of example, 156 micro-lens arrays 12 in total with 5616 micro-lenses 15.

Each micro-lens 15 of the micro-lens array 12 is connected to an optical fiber 16, the optical fiber 16 merging into fiber bundles 17. Each micro-lens 15 is connected to a photo-detector (not shown) or to a light source (not shown) via an optical fiber 16.

Figure 3B:
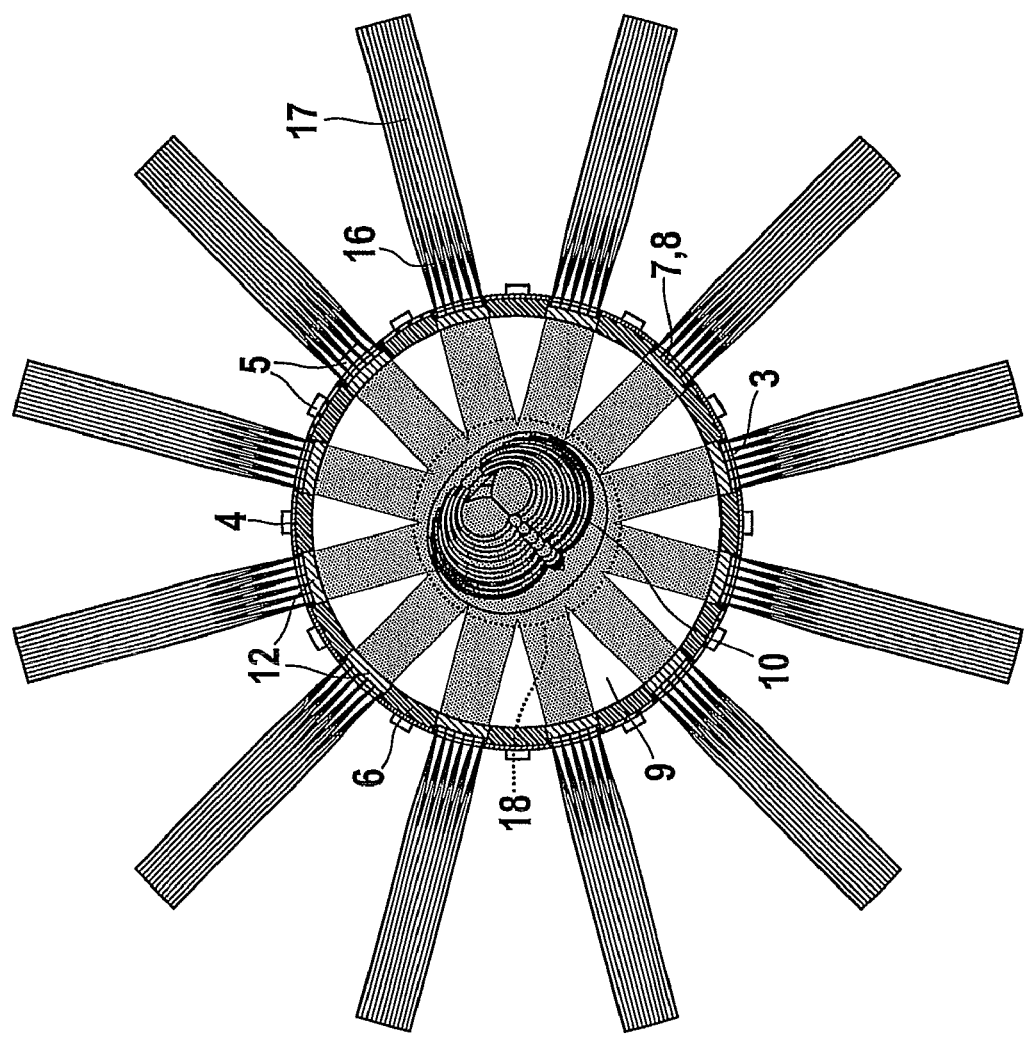

FIG. 3B shows schematically a cross section of the embodiment of the dual-modality imaging system according to FIG. 3A.

In this illustration, the components of the dual-modality imaging system as shown in FIG. 3A (micro-lens arrays 12, optical fibers 16, fiber bundle 17, straight segments 4 of the RF coil on the support 6) which surround the imaged object 10 can be seen. The RF coil and the micro-lens arrays 12 of this embodiment are arranged to generate a contiguous and overlapping field-of-view (FOV) for imaged objects 10 of a diameter smaller than the marked circle 18 (e.g. a diameter smaller than 25 mm if the diameter of the support 6 surrounding the object space 9 is 50 mm).

Figure 4:
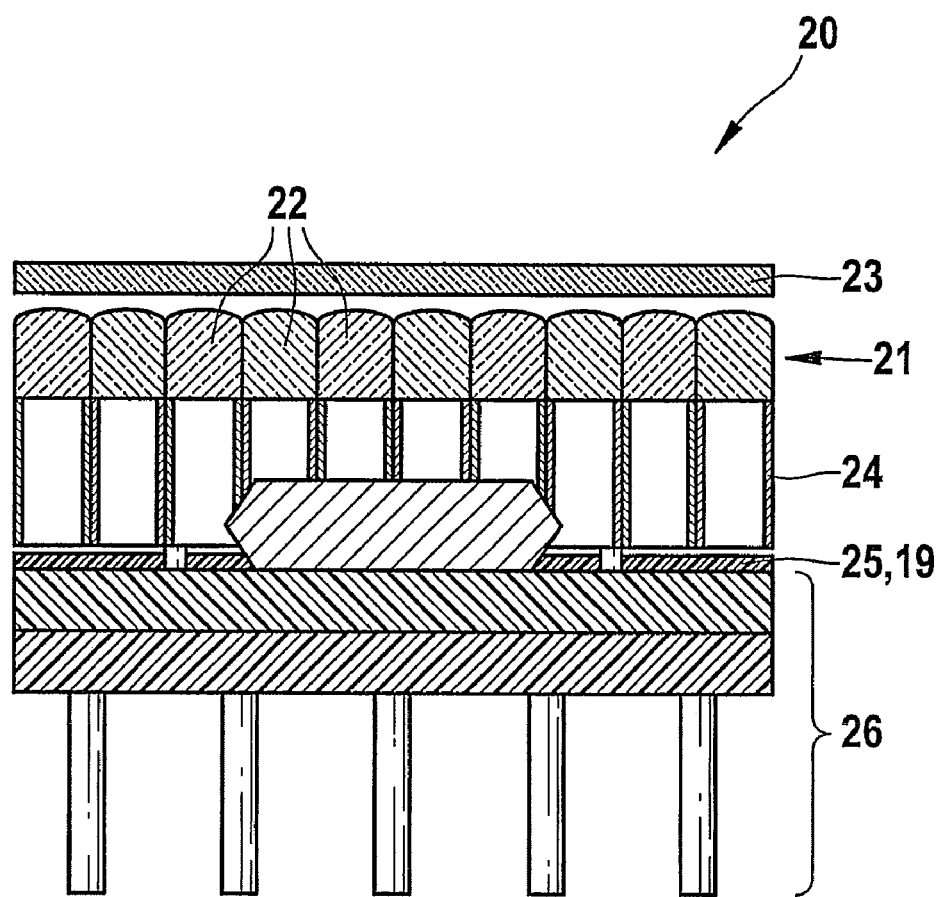
FIG. 4 shows an optical imaging detector, which can be part of an embodiment of the dual-modality imaging system according to the invention.

FIG. 4 shows an optical imaging detector, which can be part of the dual-modality imaging system according to the invention.

The figure shows a cross-section of a detector block 20. An optical imaging detector of the dual-modality imaging system according to the present invention can comprise one such detector block 20 or a plurality of detector blocks 20. The detector block 20 contains a micro-lens array 21 with a plurality of micro-lenses 22, which are arranged in a two-dimensional lattice. Preferably all micro-lenses 22 have identical geometrical and optical properties, but if necessary for an application, these properties can vary with reference to the individual micro-lenses 22 of the micro-lens array 21. The diameter of the micro-lenses 22 is chosen based upon application-required spatial resolution properties. Exemplarily lens diameters of 0.48 mm can be selected.

The detector block 20 further comprises a filter 23 positioned in front of the micro-lens array 21. The filter 23 is that part of the detector block 20, which is closest to the imaged object (not shown). The micro-lens array 21 is mounted behind the filter 23 in radial extension to the imaged object. The filter 23 is provided e.g. for filtering out excitation light when the detector block 20 is used for fluorescence imaging. The filter 23 is not needed for bioluminescence imaging.

On the other side of the micro-lens array 21 an optical collimator 24 is positioned in front of the micro-lens array 21. This photo resist collimator 24 has preferably a hole order and pitch similar to the micro-lens order and pitch of the micro-lens array 21. The collimator 24 is provided to avoid crosstalk between individual fields-of-view of the micro-lenses 22. The thickness of the collimator 24 in radial extension depends upon the space between the back facing surface of the micro-lens array 21 and the virtual focal plane of the micro-lenses 22.

Next to the collimator 24 a large-field photo detector 25 is mounted. The photo detector 25 is positioned at the focal plane of the micro-lens array 21. This photo detector 25 can be a CCD based detector, an APD array, a photo diode array, a CMOS sensor and any other position sensitive light detector. Preferably the photo detector 25 is a CMOS sensor, which shows many advantages in view of its performance (sensitivity, noise characteristics, time resolution, etc.) and in view of its cost. The photo detector 25 transforms the incoming light, which passes the filter 23, the micro-lens array 21 and the optical collimator 24, into an electrical signal.

The micro-lenses 22 of the micro-lens array 21 are distanced by a certain pitch, which should be equal to or a multitude of the photo detector's 25 pitch in order to avoid Moiré artifacts in the acquired image. Exemplarily in one experimental setup micro-lenses 22 are used with a lens diameter equal to lens pitch of 0.48 mm. The pitch of an employed CMOS sensor is chosen to be 1/10 of this (0.048 mm). The photo detector 25 is a position sensitive sensor consisting of a two-dimensional lattice of individual sensor elements. The detection effective size of one detector block 20 comprising filter 23, micro-lens array 21, collimator 24, photo detector 25, can be chosen to be e.g. 79.2 mm (axially)×5.79 mm. The micro-lens diameter can be chosen to be 0.480 mm, the micro-lens array 21 yielding 165 (axially)×12 micro-lenses 22, packed in a parallel lattice. This geometry is chosen to be a multiple of the unit of an individual photo detector element of the CMOS 19, which is e.g. 0.048 mm×0.048 mm.

The overall planar (i.e. field-of-view) dimensions of all previously described detector parts 21, 23, 24 and 25 used for image formation and detection should be equal. That is, if the size of a micro-lens array 21 is chosen to delineate a field-of-view of 1 cm×1 cm so should be the sizes of the sensor 25, collimator 24 and filter 23 as well. This is, however, not required for the sole purpose of detection. In principle, detector parts 21, 23 and 24 might be replaceable allowing for modification of imaging characteristics. If additional electronics parts and signal transmission elements 26 are necessary, as in the shown CMOS 19 design, these should be placed outside of the detector's field-of-view (also out of the MRI field-of-view).

The detector block 20 of FIG. 4 can either be used for two-dimensional (i.e. planar) or, if assembled or rotated in a certain manner, for fully 3-dimensional tomographic imaging. In most application scenarios a detector block 20 is positioned at a certain distance, but not in contact with the imaged object, with its micro-lens array detector surface oriented orthogonal to the imaged object or portions thereof. The sensitive size of such a detector block 20 can be selected arbitrarily (being constrained by technological processes) but should be governed by the size of the imaged object or portions of it.

Figure 5A:
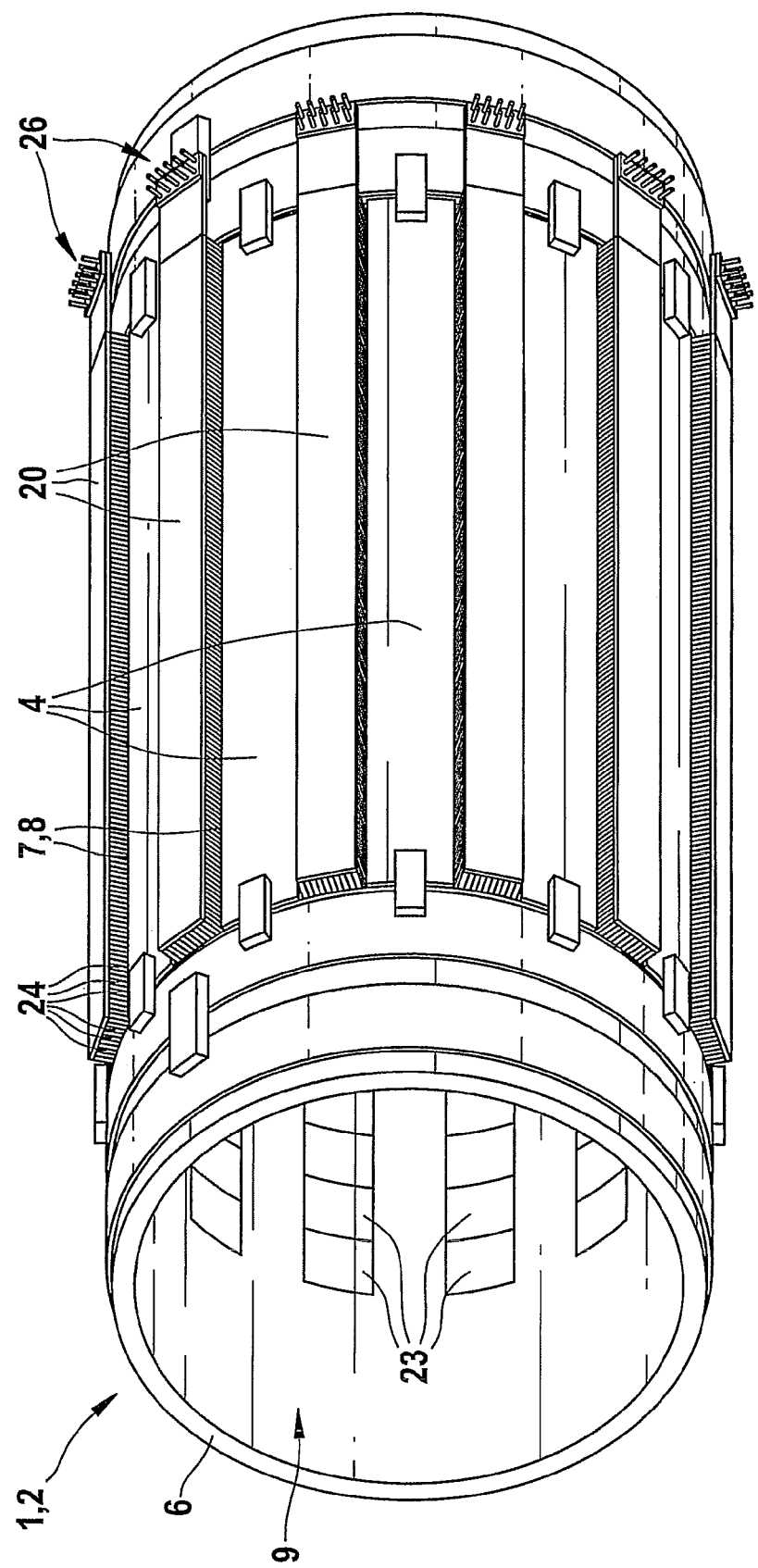
FIGS. 5A and 5B show schematically a perspective view and a transaxial view of a section of a second embodiment of the dual-modality imaging system according to the invention with micro-lens arrays and position-sensitive photo detectors located at the focal planes of the micro-lens arrays.

FIG. 5A shows schematically a perspective view of a section of a second embodiment of the dual-modality imaging system according to the invention with micro-lens arrays and position-sensitive photo detectors according to FIG. 4 located at the focal planes of the micro-lens arrays.

The shown section is part of a dual-modality imaging system, wherein an MRI apparatus for acquiring MRI data and optical imaging detectors for acquiring optical imaging data are arranged to acquire the MRI data and the optical imaging data of an imaged object (not shown) simultaneously, the optical imaging detectors being non-contact optical imaging detectors. In FIG. 5A an RF coil 1 (in a birdcage coil design 2 according to FIG. 1) which is part of the MRI apparatus is shown. In the dual-modality imaging system according to the invention this RF coil 1 is placed within the imaging volume of the MRI apparatus inside of an imaging magnet (not shown) and of gradient coils (not shown). The RF coil 1 is arranged to surround an imaged object which is placed inside of the object space 9 within the RF coil 1. Detector blocks 20 containing micro-lens arrays (not visible), which are sub-systems of the optical imaging detectors, are arranged within the imaging volume of the MRI apparatus to detect fluorescence or bioluminescence photons emitted by an imaged object through the recesses 8 (gap 7) of the RF coil 1. More precisely, the detector blocks 20 including the micro-lens arrays of the optical imaging detectors are integrated into the RF coil 1. They are localized within the gap 7 of the support 6 between the straight segments 4 of the RF coil 1. Optical fibers are not necessary for this optical imaging detector design, because the position-sensitive photo detectors of the detector blocks 20 are each positioned at the focal plane of a micro-lens array.

Figure 5B:
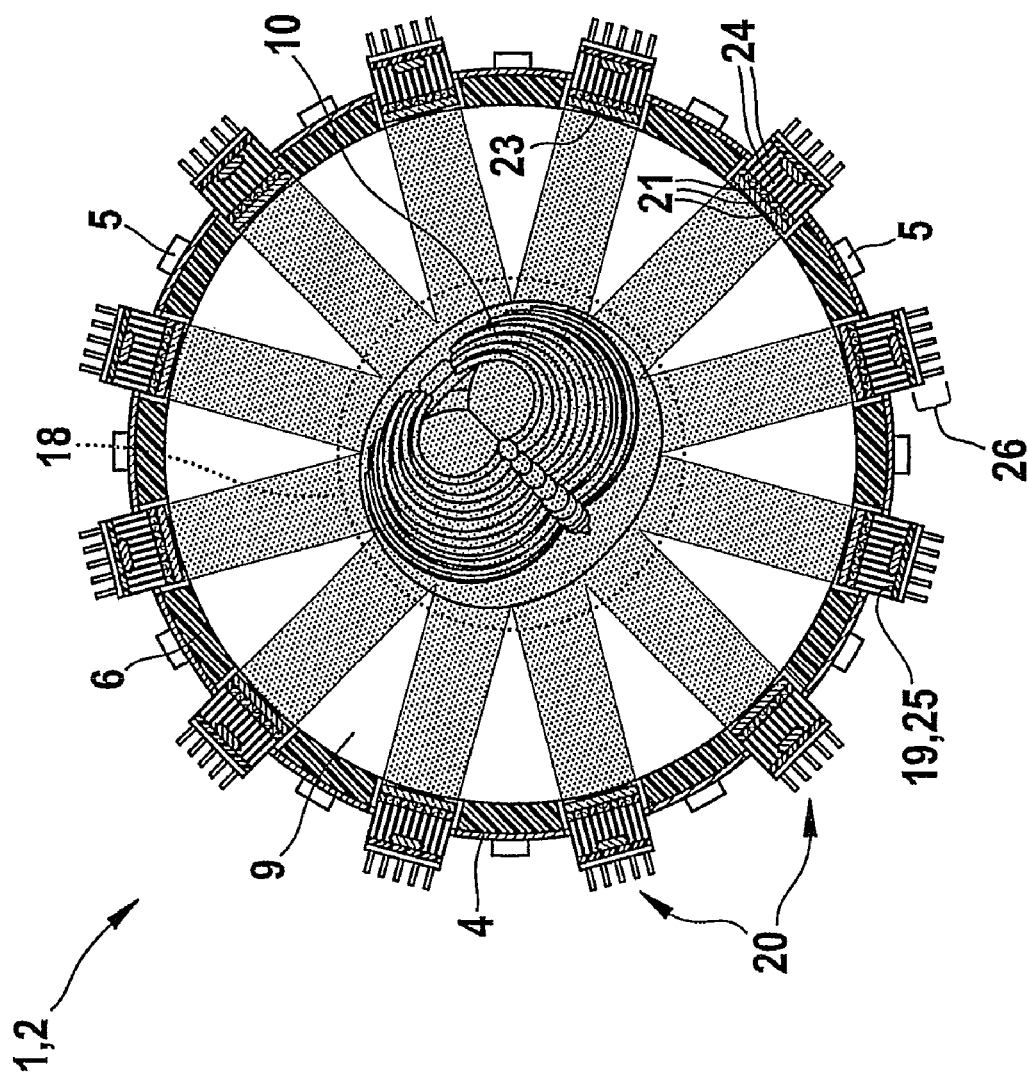

FIG. 5B shows schematically a cross-section of the embodiment of the dual-modality imaging system according to FIG. 5A.

In this illustration the components of the dual-modality imaging system as shown in FIG. 5A (the detector blocks 20, each comprising filter 23, micro-lens array 21, optical collimator 24, CMOS 19 (photo detector 25) and electronic parts and signal transmission elements 26, the straight segments 4 of the RF coil on the support with capacitors 5) which surround the imaged object 10 can be seen. The RF coil and the detector blocks 20 of this embodiment are arranged to generate a contiguous and overlapping field-of-view (FOV) for imaged objects 10 of a diameter smaller than the marked circle 18 (e.g. a diameter smaller than 25 mm if the diameter of the support surrounding the object space 9 is 50 mm).

Figure 6:
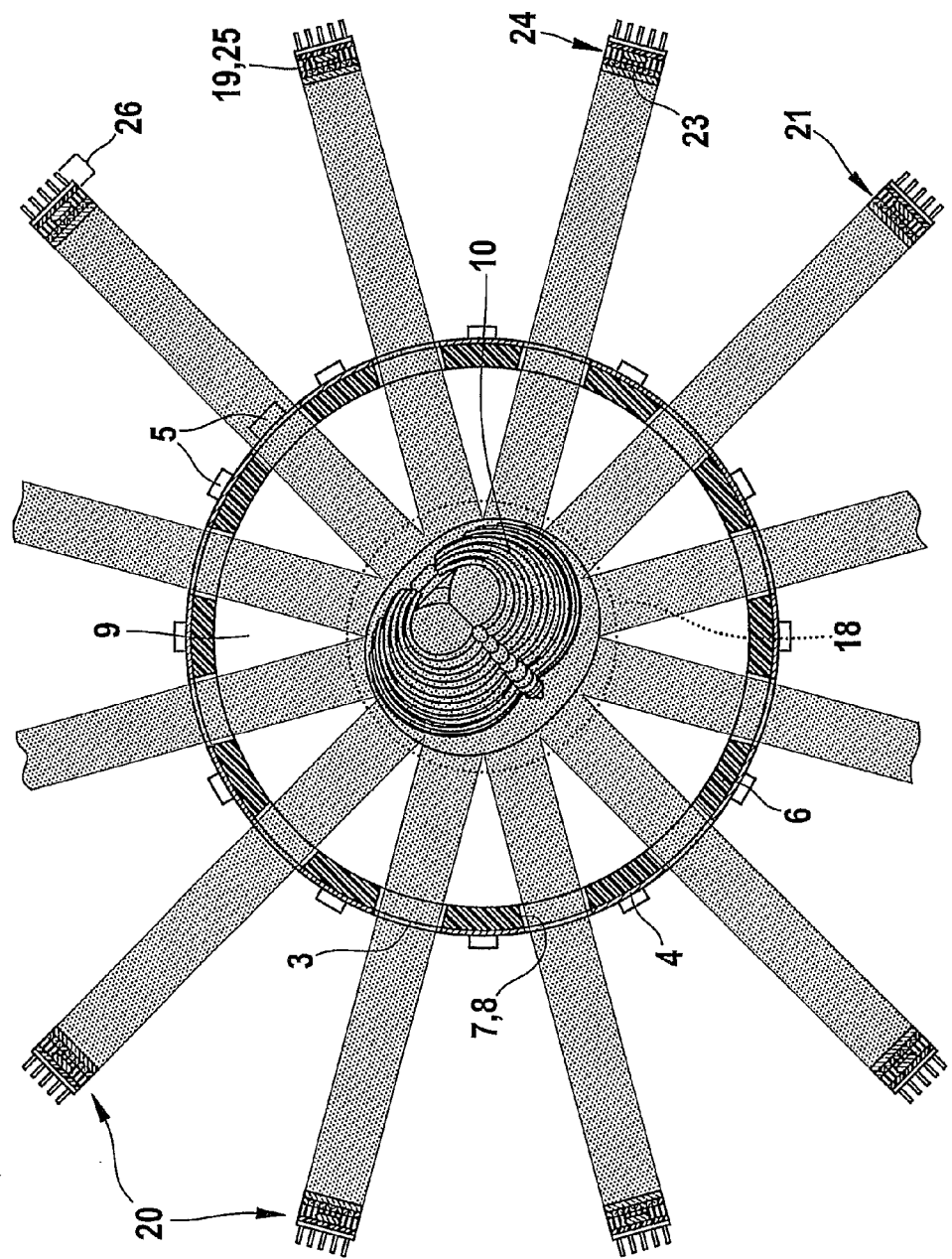
FIG. 6 shows a transaxial view of a system similar to the one shown in FIGS. 5A and 5B, where the detector blocks are radially displaced.

FIG. 6 shows a transaxial view of a system similar to the one shown in FIGS. 5A and 5B, where the detector blocks are radially displaced.

In this figure those components which are the same as in FIG. 5B are labelled by the same reference numbers. The detector blocks 20 of this embodiment are located at an increased radial distance compared to those of FIG. 5B. Such a design might be desired to reduce artifacts (if any) imposed by the materials of the detector blocks 20 onto the MRI system.

Figure 7A:
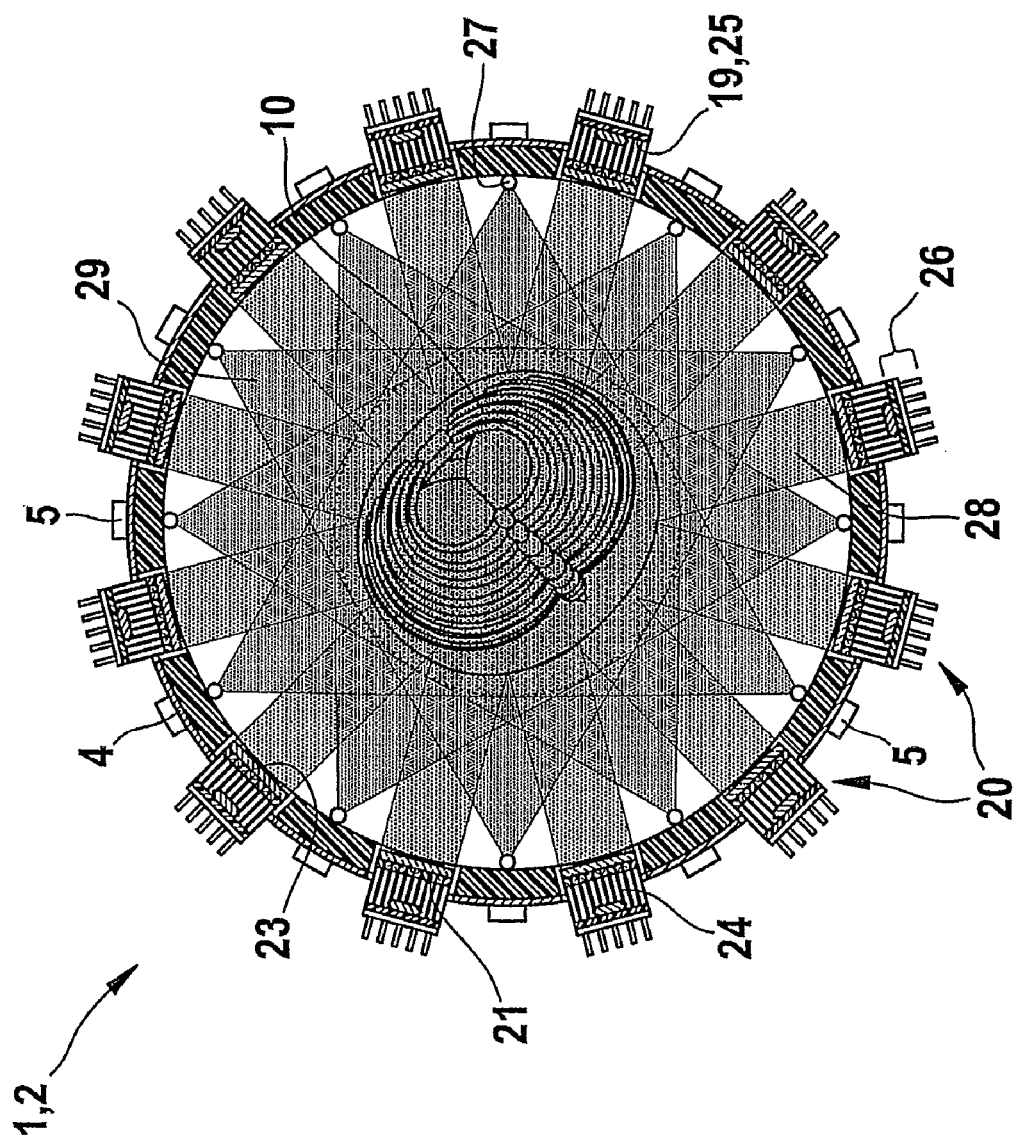
FIGS. 7A and 7B show schematically a transaxial view and a perspective view of a third embodiment according to the invention with additional light sources incorporated into the system as shown in FIGS. 5A and 5B.
Figure 7B:
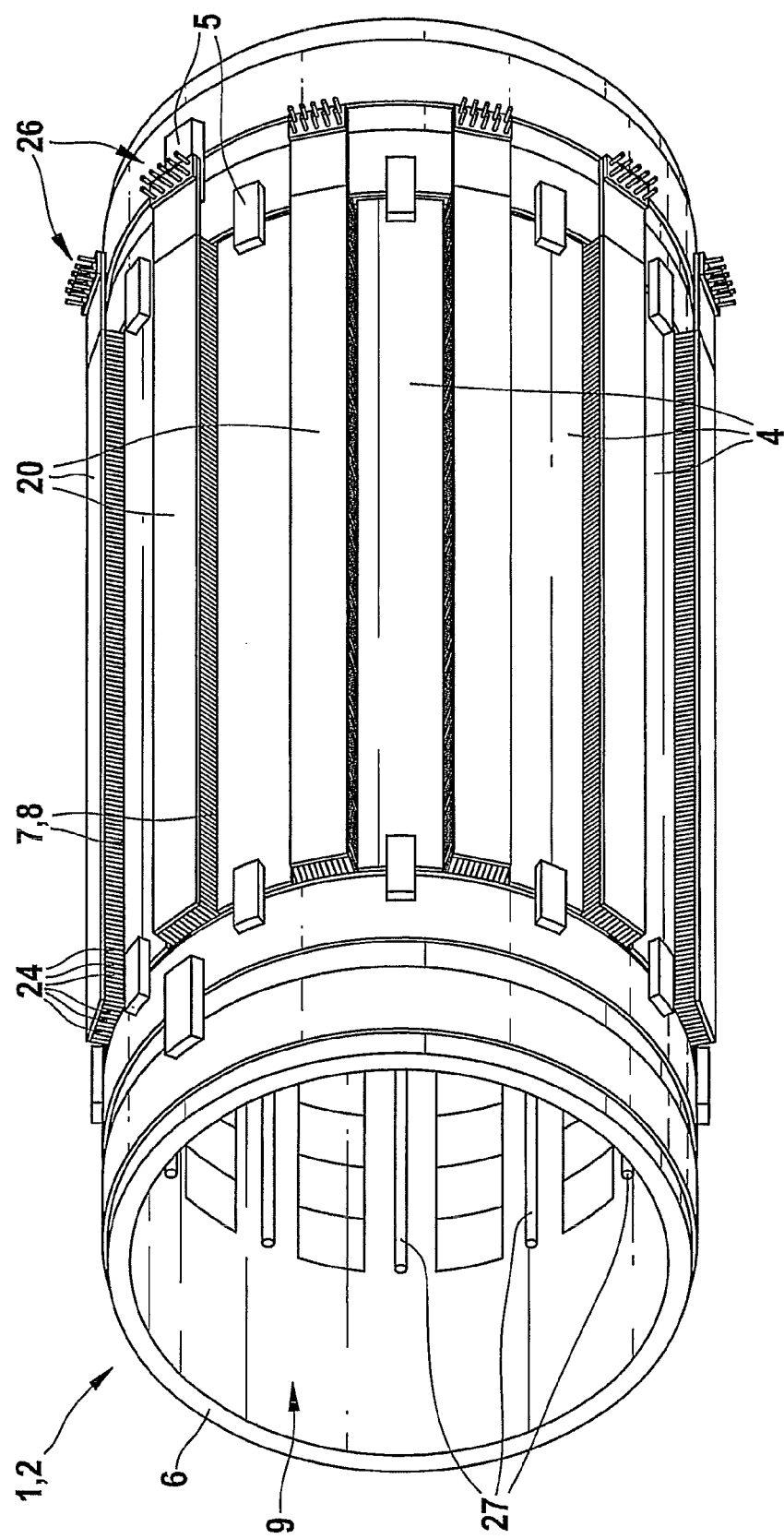

FIGS. 7A and 7B show schematically a cross section and a perspective view of a third embodiment according to the invention with light sources incorporated into a system as shown in FIGS. 5A and 5B.

In these figures those components which are the same as in FIGS. 5A and 5B are labelled by the same reference numbers. Additionally, collimated light sources are integrated into the dual-modality imaging system according to the invention. Fluorescence mediated optical imaging requires light sources 27 of variable selectable wavelengths. The fields-of-view 28 of the detector blocks 20 and the fields of light 29 of the light sources 27 overlap in the region of the imaged object 10.

It is emphasized that the RF coil 1 having a bird cage coil design is meant as an example only. In principle, each coil design is suitable for the present invention as long as enough open spaces for the detection of optical projections by means of said optical detectors are given. Still further, it is conceivable to integrate at least one optical light diffuser 27 into the at least one RF coil 1, i.e. into an appropriate space thereof. This allows for large-field-image objection illumination. This serves the purpose of fluorochrome excitation whereby the optical light diffuser 27 is part of or connected through an optical fiber to an externally arranged light source. Still further, at least one optical light beam either being a collimated laser beam or being a light transmission through an optical fiber is guided through gaps between optical photo detectors 25. This allows for narrow field or spot object illumination having the purpose of fluorochrome excitation. The at least one optical light beam can be positioned freely in respect to actual direction thereof for arbitrary illumination location on the imaged object. An azimuthal positioning is given by a rotatable gantry.

The said rotatable gantry allows for an arrangement of the at least one optical imaging detector 25, the at least one RF coil 1 and the at least one light source on a common support. By this arrangement, the relative positioning of said components remains fixed and requires no adjustment on operation of said dual-modality imaging system according to the present invention.

REFERENCE NUMBERS

1 RF coil
2 birdcage coil design
3 circular end rings
4 straight segments
5 capacitors
6 support
7 gaps
8 recesses
9 object space
10 imaged object
11 electrically conductive elements
12 micro-lens array
13 square pattern
14 multi-hole plate
15 micro-lenses
16 optical fibers
17 fiber bundle
18 circle
19 CMOS
20 detector block
21 micro-lens array
22 micro-lenses
23 filter
24 optical collimator
25 photo detector
26 electronic parts and signal transmission elements
27 light sources
28 field-of-view
29 field of light

The invention claimed is:

1. A dual-modality imaging system, wherein a magnetic resonance imaging (MRI) apparatus for acquiring MRI data and at least one optical imaging detector for acquiring optical imaging data are arranged to acquire the MRI data and the optical imaging data of an imaged object simultaneously, the at least one optical imaging detector being a non-contact optical imaging detector and wherein the MRI apparatus comprises an imaging magnet to produce a static magnetic field within an imaging volume of the MRI apparatus, gradient coils to produce gradient magnetic fields to superimpose the static magnetic field within the imaging volume and at least one radio frequency (RF) coil, which is arranged within the imaging volume to surround the imaged object, at least a subsystem of the at least one optical imaging detector being arranged within the imaging volume to detect photons emitted by the imaged object through a recess of the RF coil, characterized in that the at least one optical imaging detector comprises a micro-lens array with a plurality of micro-lenses, the micro-lens array being integrated into the at least one RF coil.

2. The dual-modality imaging system according to claim 1, wherein at least a subsystem of the optical imaging detector is integrated into the at least on RF coil forming a module, which is permanently integrated into the MRI apparatus or which is removably combined with the MRI apparatus.

3. The dual-modality imaging system according to claim 1, wherein the RF coil has a birdcage coil design.

4. The dual-modality imaging system according to claim 1, wherein each micro-lens is connected to an optical fiber.

5. The dual-modality imaging system according to claim 1, wherein each micro-lens is connected to an optical fiber and wherein each micro-lens is connected to a photo detector or to a light source via the optical fiber.

6. The dual-modality imaging system according to claim 1, wherein the at least one optical imaging detector comprises at least one photo detector.

7. The dual-modality imaging system according to claim 1, wherein the at least one optical imaging detector comprises a position-sensitive photo detector.

8. The dual-modality imaging system according to claim 1, wherein the at least one optical imaging detector comprises a position-sensitive photo detector and wherein the at least one optical imaging detector comprises a micro-lens array and the position-sensitive photo-detector is positioned at the focal plane of a micro-lens array.

9. The dual-modality imaging system according to claim 1, wherein the at least one optical imaging detector comprises a position-sensitive photo detector and wherein the position-sensitive photo-detector is at least one sensor selected from the group of charge-coupled device (CCD) based detector, avalanche photo diode (APD) array, photo diode array or complementary metal-oxide semiconductor (CMOS) sensor.

10. The dual-modality imaging system according to claim 1, wherein at least one optical light diffuser is integrated into the at least one RF coil (or into appropriate free space) for large-field imaged object illumination (having the purpose of fluorochrome excitation), whereby the optical light diffuser is part of or connected through an optical fiber to an externally placed light source.

11. The dual-modality imaging system according to claim 1, wherein at least one optical light beam, either collimated laser beam or light transmission through optical fiber, is guided through gaps between optical photo detectors for narrow-field or spot object illumination, having the purpose of fluorochrome excitation, the at least one optical light beam being positioned freely in axial direction for arbitrary illumination location upon the imaged object.

12. The dual-modality imaging system according to claim 1, wherein the at least one imaging detector, the at least one RF coil and the at least one light source are mounted on a common rotatable gantry.

13. The dual-modality imaging system according to claim 1, wherein the at least one imaging detector, the at least one RF coil and the at least one light source are mounted on a common rotatable gantry, and wherein the azimuthal position is provided by the rotatable gantry.

14. A method for dual-modality imaging of an imaged object, the method comprising:
  acquiring magnetic resonance imaging data and optical imaging data of the imaged object simultaneously using a magnetic resonance imaging (MRI) apparatus and a non-contact optical imaging detector, wherein
    the MRI apparatus comprises an imaging magnet to produce a static magnetic field within an imaging volume of the MRI apparatus, gradient coils to produce gradient magnetic fields to superimpose the static magnetic field within the imaging volume and at least one radio frequency (RF) coil, which is arranged within the imaging volume to surround the imaged object,
    at least a subsystem of the at least one optical imaging detector being arranged within the imaging volume to detect photons emitted by the imaged object through a recess of the RF coil, and wherein;
    the optical imaging data is acquired using at least one optical imaging detector comprising a micro-lens array with a plurality of micro-lenses, the micro-lens array being integrated into the at least one RF coil; and
  generating at least one image from the acquired data.

15. The method of claim 14, and further including the steps of:
reconstructing a magnetic resonance (MR) image and an optical image using the acquired MRI data and optical imaging data and;
displaying at least one of the MR image, the optical image or a fused MR/optical image on a display device.

* * * * *